(12) United States Patent
Bedwell et al.

(10) Patent No.: US 7,749,971 B2
(45) Date of Patent: Jul. 6, 2010

(54) AMINOGLYCOSIDE TREATMENT FOR LYSOSOMAL STORAGE DISEASES

(76) Inventors: David M. Bedwell, 2143 Woodledge Dr., Birmingham, AL (US) 35226; Kim M. Keeling, 665 Idlewild Cir., Apt. A-23, Birmingham, AL (US) 35205

( * ) Notice: Subject to any disclaimer, the term of this patent is extended or adjusted under 35 U.S.C. 154(b) by 1001 days.

(21) Appl. No.: 10/079,326

(22) Filed: Feb. 20, 2002

(65) Prior Publication Data

US 2005/0153906 A1   Jul. 14, 2005

Related U.S. Application Data

(60) Provisional application No. 60/270,092, filed on Feb. 20, 2001.

(51) Int. Cl.
  *A61K 31/70*   (2006.01)
(52) U.S. Cl. .............. 514/35; 514/36; 514/37; 514/38; 514/39; 514/40; 514/41
(58) Field of Classification Search .............. 514/35, 514/36, 37, 38, 39, 40, 41
See application file for complete search history.

(56) References Cited

U.S. PATENT DOCUMENTS

| | | | | |
|---|---|---|---|---|
| 4,526,888 A | * | 7/1985 | Williams et al. | 514/12 |
| 5,310,646 A | | 5/1994 | Whitley | 435/4 |
| 5,677,288 A | * | 10/1997 | Marangos | 514/39 |
| 6,426,208 B1 | * | 7/2002 | Kakkis et al. | 435/201 |
| 6,475,993 B2 | * | 11/2002 | Tremblay | 514/37 |

OTHER PUBLICATIONS

Keeling et al, Chemical Abstracts 138-130644 CA, Journal of Molecular Medicine (Berlin, Germany) (2002), 80 (6), 367-376.*

* cited by examiner

*Primary Examiner*—Elli Peselev
(74) *Attorney, Agent, or Firm*—Bradley Arant Boult Cummings, LLP

(57) ABSTRACT

The present invention provides a method of treating lysosomal storage diseases such as Hurler syndrome and Batten disease in individuals in need of such treatment, comprising the step of administering to said individuals a therapeutically effective dose of an aminoglycoside. In addition, this method may further comprise treating the individual with enzyme replacement therapy. Furthermore, the present invention provides method of pharmacologically suppressing premature stop mutations in an individual with these lysosomal storage diseases, comprising the step of administering to said individual a pharmacologically effective dose of an aminoglycoside.

17 Claims, 10 Drawing Sheets

SEQUENCE LISTING

<160> NUMBER OF SEQ ID NOS: 8

<210> SEQ ID NO 1
<211> LENGTH: 6
<212> TYPE: DNA
<213> ORGANISM: artificial sequence
<220> FEATURE:
<223> OTHER INFORMATION: Nucleotide sequence of NsiI site replacing the
      HindIII in pDB603 to construct plasmid pDB650

<400> SEQUENCE: 1 atgcat                                                                     6

<210> SEQ ID NO 2
<211> LENGTH: 36
<212> TYPE: DNA
<213> ORGANISM: artificial sequence
<220> FEATURE:
<221> NAME/KEY: primer
<223> OTHER INFORMATION: Nucleotide sequence of primer DB843

<400> SEQUENCE: 2
gtcgacctgc agcccatgca tggcgtaatc atggtc                                   36

<210> SEQ ID NO 3
<211> LENGTH: 36
<212> TYPE: DNA
<213> ORGANISM: artificial sequence
<220> FEATURE:
<221> NAME/KEY: primer
<223> OTHER INFORMATION: Nucleotide sequence of primer DB844

<400> SEQUENCE: 3
gaccatgatt acgccatgca tgggctgcag gtcgac                                   36

<210> SEQ ID NO 4
<211> LENGTH: 39
<212> TYPE: DNA
<213> ORGANISM: artificial sequence
<220> FEATURE:
<223> OTHER INFORMATION: Synthetic restriction fragment containing
      Q70X TAG stop mutation and six codons of
      flanking upstream and downstream IDUA context

<400> SEQUENCE: 4
tacgtcctca gctgggacta gcagctcaac ctcgcctat                                39

<210> SEQ ID NO 5
<211> LENGTH: 6
<212> TYPE: PRT
<213> ORGANISM: artificial sequence
<220> FEATURE:
<223> OTHER INFORMATION: Amino acid sequence coded by IDUA codons
      upstream of Q70X TAG stop mutation

<400> SEQUENCE: 5

Tyr Val Leu Ser Trp Asp
              5

<210> SEQ ID NO 6
<211> LENGTH: 6
<212> TYPE: PRT
<213> ORGANISM: artificial sequence
<220> FEATURE:
<223> OTHER INFORMATION: Amino acid sequence coded by IDUA codons
      downstream of Q70X TAG stop mutation

```
<400> SEQUENCE: 6

Gln Leu Asn Leu Ala Tyr
                    5

<210> SEQ ID NO 7
<211> LENGTH: 47
<212> TYPE: DNA
<213> ORGANISM: artificial sequence
<220> FEATURE:
<223> OTHER INFORMATION: Nucleotide sequence of oligonucleotide DB863

<400> SEQUENCE: 7
gatcctacgt cctcagctgg gactagcagc tcaacctcgc ctatgca                47

<210> SEQ ID NO 8
<211> LENGTH: 47
<212> TYPE: DNA
<213> ORGANISM: artificial sequence
<220> FEATURE:
<223> OTHER INFORMATION: Nucleotide sequence of oligonucleotide DB864

<400> SEQUENCE: 8
agcttgcata ggcgaggttg agctgctagt cccagctgag gacgtag                 47
```

AMINOGLYCOSIDE TREATMENT FOR LYSOSOMAL STORAGE DISEASES

CROSS-REFERENCE TO RELATED APPLICATION

This non-provisional patent application claims benefit of provisional patent application U.S. Ser. No. 60/270,092, filed Feb. 20, 2001, now abandoned.

FEDERAL FUNDING LEGEND

This invention was produced in part using funds from the Federal government under NIH grant DK53090. Accordingly, the Federal government has certain rights in this invention.

SEQUENCE LISTING

This application contains a Sequence Listing, a copy of which is submitted herewith in compliance with 37 C.F.R. 1.821 and is incorporated by reference herein. One (1) compact disc is submitted herein. The file on said compact disc is "D6394SEQ" and is 2 kb in size. The file was created on Jul. 8, 2004.

BACKGROUND OF THE INVENTION

1. Field of the Invention

The present invention relates generally to molecular pharmacology and therapeutics of lysosomal storage diseases. More specifically, the present invention relates to methods of using aminoglycoside antibiotics to treat mucopolysaccharidosis I (particularly Hurler Syndrome) and Batten disease.

2. Description of the Related Art

The lysosome is the cellular compartment that facilitates the degradation of macromolecules in the cell that have outlived their usefulness to the cell. Because of this important degradative role, many hydrolytic enzymes required to carry out the destruction of these surplus macromolecules reside in the lysosome. When one or more of these enzymes is missing, their substrates can no longer be degraded and accumulate, leading to a series of disorders that are frequently referred to as lysosomal storage diseases.

The term mucopolysaccharidoses describes a class of lysosomal storage disorders that are characterized by the excessive accumulation of glycosaminoglycans (GAGs) within the lysosomes of various tissues. Among these disorders, mucopolysaccharidosis I (MPS I) is an autosomal recessive lysosomal storage disease caused by a loss of the enzyme α-L-iduronidase, which participates in the degradation of glycosaminoglycans within the lysosome. Mucopolysaccharidosis I can be further subdivided into three categories: Hurler (MPS I-H), the most severe form; Scheie (MPS I-S) a mild form; and Hurler/Scheie (MPS I-H/S), an intermediate form. Hurler syndrome is characterized by a near total absence of α-L-iduronidase activity, leading to the accumulation of both dermatan and heparan sulfate within the lysosomes (6). Physical symptoms of the disease include stiffness in joints, skeletal abnormalities and corneal clouding. Progression of Hurler syndrome results in heart and liver disease as well as mental deterioration, with death usually occurring in childhood (7).

The two most frequent mutations found in MPS I patients with Hurler syndrome, the Q70X and W402X nonsense mutations, are present in ~70% of patients of European descent (8). Significantly, the other forms of MPS I present clinically with milder symptoms, suggesting that much of the disease phenotype can be alleviated by as little as 1% of normal α-L-iduronidase activity (9-11).

Another group of lysosomal storage diseases which may benefit from the novel use of aminoglycosides for suppression therapy are the neuronal ceroid lipofuscinoses (NCLs), also collectively known as Batten disease. The neuronal ceroid lipofuscinoses are the most common childhood neurodegenerative disease with an incidence of 1 in 100,000. All types of neuronal ceroid lipofuscinoses are inherited in an autosomal recessive manner. Symptoms of neuronal ceroid lipofuscinoses include visual loss, seizures, paralysis, dementia, and premature death. The neuronal ceroid lipofuscinoses can be subdivided into four major types based upon the age of onset: infantile, late infantile, juvenile, and adult. In addition, the type of accumulating material within the lysosomes varies among the different forms of neuronal ceroid lipofuscinosis. Specifically, at least eight genes underlie the neuronal ceroid lipofuscinoses, four of which have been isolated and the mutations that cause neuronal ceroid lipofuscinosis characterized. These include CLN1, CLN2, CLN3, and CLN5. Mutations in CLN2 are associated with the late infantile onset form of neuronal ceroid lipofuscinosis. CLN2 has been found to contain the most nonsense mutations among the NCLs (26% of the characterized alleles)[*Hum. Mut.* 14: 199-215, 1999]. The protein encoded by CLN2 is tripeptidyl-peptidase I (TTP1) which functions in degradation of proteins within the lysosome. Without this enzyme, selected proteins accumulate within the lysosomes, with the major component of the accumulation products being an extremely hydrophobic subunit of the mitochondrial ATP synthase. The lysosomal accumulation of this type of storage product causes the onset of the late infantile form of neuronal ceroid lipofuscinosis. [*Biochim. Biophys. Acta* 1429: 496-500, 1999; *J. Neurochem.* 72: 2573-2582, 1999]. Aminoglycosides will be utilized to suppress premature stop mutations within the CLN2 gene in order to restore sufficient levels of TTP1, and alleviate the disease phenotype. This approach may be used prior to or contemporaneously with treatment consisting of the administration of recombinantly produced TTP1 and/or a CLN2 gene therapy vector [J. Neurochem. 73: 700-711, 1999].

Other studies have shown that aminoglycosides can also suppress premature stop mutations in other non-lysosomal diseases at levels that restore physiologically relevant amounts of functional protein. The utility of this approach was first demonstrated with the autosomal recessive disease cystic fibrosis (CF), where the aminoglycosides gentamicin and G418 were shown to suppress nonsense mutations in the CF-transmembrane conductance regulator (CFTR) gene (1,2). These compounds were shown to suppress a genomic cystic fibrosis nonsense mutation in a human bronchial epithelial cell line, restoring both CFTR protein localized to the apical plasma membrane and its cAMP-activated chloride channel activity. The specificity of aminoglycoside action for nonsense suppression was shown in these studies since cells homozygous for the ΔF508 CFTR allele did not respond to aminoglycoside treatment. More recently, clinical data obtained in pilot studies with cystic fibrosis patients carrying nonsense mutations indicated that topical or intravenous gentamicin can partially restore CFTR activity in vivo (3,4). Another study found that gentamicin can also suppress a nonsense mutation in the dystrophin (Dmd) gene of the mdx mouse, which represents an animal model for Duchenne muscular dystrophy (5). The partial restoration of dystrophin expression was accompanied by a significant decrease in muscular deterioration in treated animals. However, the ability of aminoglycosides to suppress stop mutations and reverse the biochemical defects associated with any other human genetic disease is highly unpredictable.

The well-defined correlation between enzymatic activity and disease severity makes the MPS I and NCL disorders good candidate diseases to examine whether the level of protein expression restored by aminoglycoside suppression of stop mutations can reverse the biochemical defects associated with a human genetic disease.

The prior art is deficient in an effective therapeutic regimen for either MPS I (such as Hurler syndrome) or the neuronal ceroid lipofuscinoses (such as Batten disease). The present fulfills this long-standing need and desire in the art to provide a treatment for these lysosomal storage diseases.

SUMMARY OF THE INVENTION

The prior art suggests that the use of aminoglycosides would not be useful to treat lysosomal storage diseases in general, since the major side effects of aminoglycoside treatment are manifested by lysosomal dysfunction (*Antimicrob. Agents Chemother.* 43: 1003-1012, 1999). The present invention demonstrates that the suppression of nonsense mutations by gentamicin can reverse the biochemical defects of Hurler syndrome, suggesting that aminoglycoside therapy (with or without a complementary therapeutic regimen) may provide an effective treatment for many patients with Hurler syndrome (as well as many other lysosomal storage diseases).

Hurler syndrome is the most severe form of a lysosomal storage disease caused by loss of the enzyme α-L-iduronidase (encoded by the IDUA gene), which participates in the degradation of glycosaminoglycans (GAGs) within the lysosome. In some populations, premature stop mutations represent roughly two-thirds of the mutations that cause Hurler syndrome. In this study, whether the aminoglycoside gentamicin can suppress stop mutations within the IDUA gene was investigated. A Hurler syndrome fibroblast cell line heterozygous for the IDUA stop mutations Q70X and W402X showed a significant increase in α-L-iduronidase activity when cultured in the presence of gentamicin, resulting in the restoration of 2.8% of normal α-L-iduronidase activity. Determination of α-L-iduronidase protein levels by an immunoquantification assay indicated that gentamicin treatment produced a similar increase in α-L-iduronidase protein in Hurler cells. Both the α-L-iduronidase activity and protein level resulting from this treatment have previously been correlated with mild Hurler phenotypes. Although Hurler fibroblasts contain a much higher level of glycosaminoglycans than normal, gentamicin treatment reduced glycosaminoglycan accumulation in Hurler cells to a normal level. Furthermore, a reduced glycosaminoglycan level could be sustained for at least 2 days after gentamicin treatment was discontinued. The reduction in the glycosaminoglycan level was also reflected in a marked reduction in lysosomal vacuolation. Taken together, these results suggest that the suppression of premature stop mutations may provide an effective treatment for Hurler syndrome patients with premature stop mutations in the IDUA gene.

In one embodiment of the present invention, there is provided a method of treating mucopolysaccharide-related storage diseases (such as Hurler syndrome) in an individual in need of such treatment, comprising the step of administering to the individual a therapeutically effective dose of an aminoglycoside.

In another embodiment of the present invention, there is provided a method of pharmacologically suppressing premature stop mutations in an individual with mucopolysaccharide-related lysosomal storage diseases (such as Hurler syndrome), comprising the step of administering to the individual a pharmacologically effective dose of an aminoglycoside.

In yet another embodiment of the present invention, there is provided a method of treating other lysosomal storage diseases caused by premature stop mutations (such as Batten Disease) in an individual in need of such treatment, comprising the step of administering to said individual a therapeutically effective dose of an aminoglycoside.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 shows gentamicin-mediated suppression of the IDUA-W402X stop mutation. DNA templates were expressed in a rabbit reticulocyte lysate coupled transcription/translation system in the presence of increasing amounts of gentamicin. Immediately following the completion of the reaction, the truncated and full-length translation products were separated by SDS-PAGE and quantitated by PhosphorImager analysis.

FIG. 4 shows the increase in α-L-iduronidase activity in Hurler fibroblasts mediated by gentamicin is sufficient to reduce glycosaminoglycan accumulation.

DETAILED DESCRIPTION OF THE INVENTION

Figure 1A:
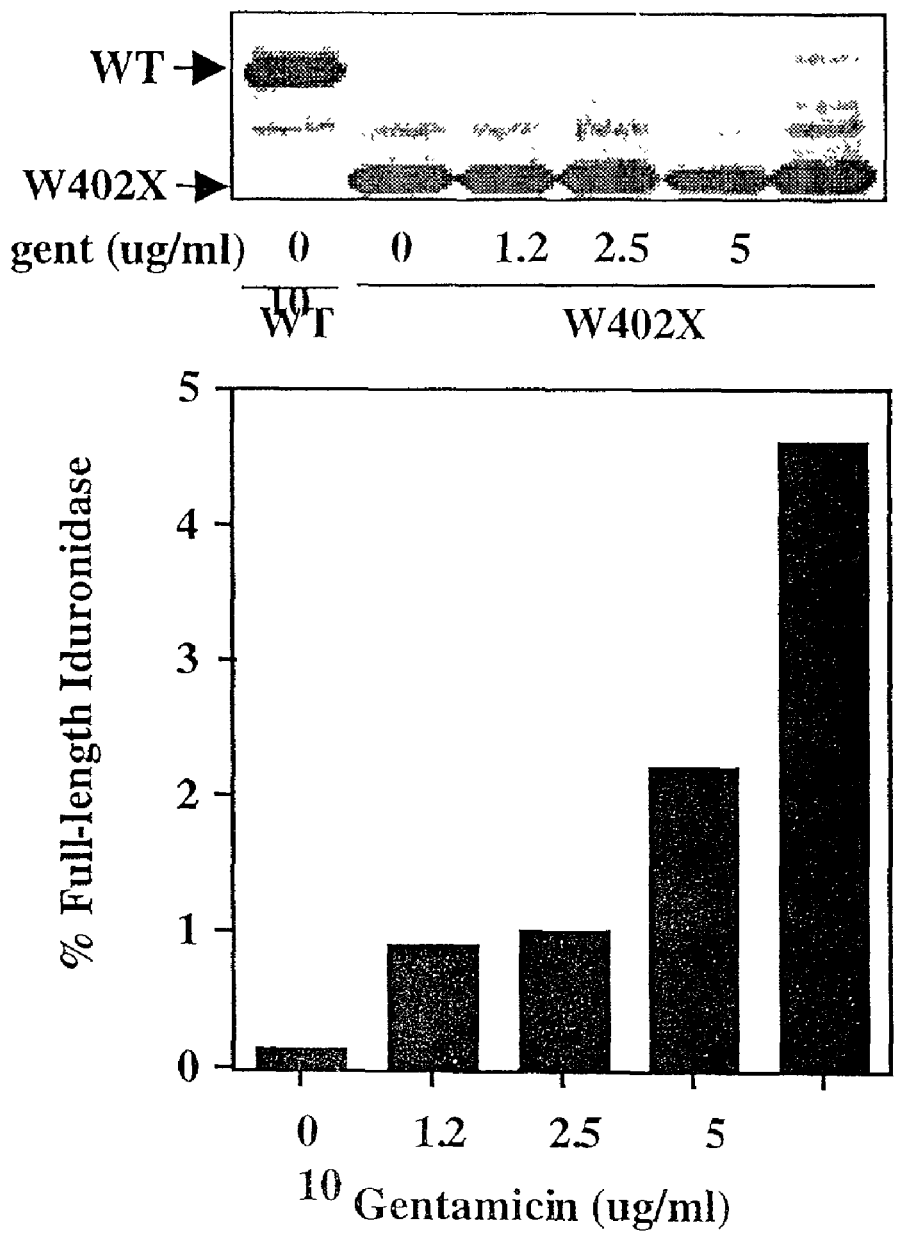
FIG. 1A shows polypeptides produced from the human IDUA-W402X cDNA when translation was carried out with increasing concentrations of gentamicin. WT, full-length α-L-iduronidase; W402X, α-L-iduronidase truncated at the premature stop mutation.

In one embodiment of the present invention, there is provided a method of treating Hurler syndrome in an individual in need of such treatment, comprising the step of administering to the to individual a therapeutically effective dose of an aminoglycoside. Representative examples of therapeutically useful aminoglycosides include gentamicin, G418, hygromycin B, paromomycin, tobramycin, lividomycin A, amikacin, sisomycin, and neomycin. Administration of these aminoglycosides is routine to a person having ordinary skill in this art. For example, gentamicin may be administered in a dose from about 1 mg/kg to about 500 mg/kg. Preferably, the aminoglycoside suppresses a naturally occurring premature stop mutation. For example, the naturally occurring premature stop mutation could be either the IDUA-Q70X stop mutation and the IDUA-W402X stop mutation. In addition, this method of treating Hurler syndrome in an individual in need of such treatment may further comprise the step of concurrently treating said individual with enzyme replacement therapy. In yet another aspect of this method, the method may further comprise the step of treating said individual with a poly-anionic compound. Representative poly-anionic compounds include poly-L-aspartic acid and daptomycin.

The present invention is also directed to a method of pharmacologically suppressing premature stop mutations in an individual with Hurler syndrome, comprising the step of administering to the individual a pharmacologically effective dose of an aminoglycoside. Representative examples of therapeutically useful aminoglycosides include gentamicin, G418, hygromycin B, paromomycin, tobramycin, lividomycin A, amikacin, sisomycin, and neomycin. Administration of an aminoglycoside is routine to a person having ordinary skill in this art. For example, gentamicin may be administered in a dose of from about 1 mg/kg to about 500 mg/kg. Preferably, the aminoglycoside suppresses a naturally occurring premature stop mutation. For example, the naturally occurring premature stop mutation could be either the IDUA-Q70X stop mutation and the IDUA-W402X stop mutation. In addition, this method of pharmacologically suppressing premature stop mutations in an individual with Hurler syndrome may further comprise the step of concurrently treating said with enzyme replacement therapy. This enzyme replacement therapy may be performed either prior to said aminoglycoside treatment, concurrently with said aminoglycoside treatment or subsequent to said aminoglycoside treatment. Preferably, the enzyme is recombinantly produced alpha-L iduronidase such as Aldurazyme®. In another aspect of this method, one may treat an individual with Hurler disease with a combination of aminoglycosides and a gene therapy vector encoding alpha-L-iduronidase. In yet another aspect of this method, the method may further comprise the step of treating said individual with a poly-anionic compound. Representative poly-anionic compounds include poly-L-aspartic acid and daptomycin.

In a preferred embodiment of the present invention, treatment with gentamicin or other aminoglycosides may be used prior to or contemporaneously with enzyme replacement therapy and/or gene therapy which utilizes DNA molecules which encode a therapeutic protein of interest, under conditions suitable for the expression of said DNA molecule. Thus, for the treatment of Hurler's Disease [also known as mucopolysaccharidosis I, or MPS-I], the methods of the present invention may be used prior to or contemporaneously with treatment with recombinantly produced alpha-L iduronidase, presently in clinical trials [Aldurazyme®, Genzyme Corporation, Cambridge, Mass. and BioMarin Pharmaceuticals, Inc, Novato, Calif.; also see Shull et al, PNAS USA 91:12937-12941 (1994)]; or with a gene therapy vector encoding recombinantly produced alpha-L-iduronidase [see PCT patent publication WO9310244, the disclosure of which is hereby incorporated herein by reference].

The present invention is also directed to a method of treating a lysosomal storage disease in an individual in need of such treatment, comprising the step of administering to said individual a therapeutically effective dose of an aminoglycoside. For example, for the treatment of Batten Disease, also known as late-infantile neuronal ceroid lipofuscinosis (LINCL), treatment with gentamicin or other aminoglycosides according to the methods of the present invention may be used prior to or contemporaneously with treatment with recombinantly produced neuronal ceroid lipofuscinose CLN2, and/or a gene therapy vector encoding the CLN2 gene. [See Sohar et al., J. Neurochemistry, 73:700-711 (1999), the disclosure of which is hereby incorporated herein by reference]. This method may also be used to treat other lysosomal storage diseases, such as mucopolysaccharidosis I, e.g., Scheie disease and Hurler/Scheie disease.

Methods for producing recombinant enzymes are well known in the art. In addition, gene therapy vectors, including both viral and non-viral based vectors, are well known. Suitable viral based vector systems include adenovirus, adeno-associated virus, and retroviruses, including lentiviruses, such as human immunodeficiency virus [HIV]. Non-viral based vector systems include cationic amphiphilic compounds and other polymeric compounds; as well as DNA in the absence of viral or non-viral compounds, known as "naked DNA." Other systems include combinations of both viral and non-viral components. In yet another aspect of this method, the method may further comprise the step of treating said individual with a poly-anionic compound. Representative poly-anionic compounds include poly-L-aspartic acid and daptomycin.

The following examples are given for the purpose of illustrating various embodiments of the invention and are not meant to limit the present invention in any fashion:

Example 1

In Vitro Transcription/Translation Reactions

Human _-L-iduronidase (IDUA) cDNAs containing either the W402X (TGG to TAG) or Q70X (CAG to TAG) mutation were expressed from the SP6 promoter in a rabbit reticulocyte lysate coupled transcription/translation system (Promega). Optimal gentamicin concentrations used for the suppression of stop mutations were similar to those described in Manouvakova et al. (12). The addition of $^{35}$S-labeled methionine to the translation reaction allowed the analysis of the translation products by SDS-PAGE and quantitation by PhosphorImager analysis. The level of suppression of the stop mutation was expressed as the amount of full-length protein produced relative to the sum of the truncated and full-length proteins. When necessary, corrections were also made for the difference in the number of methionine residues present in the truncated and full-length translation species.

The readthrough reporter plasmid pDB650, used to examine the suppression of the IDUAQ70X mutation, was derived from plasmid pDB603 (12). To make this plasmid, a HindIII site beyond the polylinker was first changed to an NsiI site (ATGCAT) (SEQ ID NO: 1). This was done using a QuikChange mutagenesis kit (Stratagene) and the primers DB843 (5'-GTC GAC CTG CAG CC ATG CAT GGC GTA ATC ATG GTC-3') (SEQ ID NO: 2) and its complement, DB844 (5'-GAC CAT GAT TAC GCC ATG CAT GGG CTG CAG GTC GAC-3' SEQ ID NO: 3). A synthetic restriction fragment containing the Q70X TAG stop mutation and six codons of flanking upstream and downstream IDUA context (SEQ ID NO: 4) was then introduced between the unique BamHI and HindIII sites located in the readthrough cassette. The synthetic DNA fragment was made by annealing the DNA oligonucleotides DB863 (5'-GAT CCT ACG TCC TCA GCT GGG ACT AGC AGC TCA ACC TCG CCT ATG CA-3') (SEQ ID NO: 7) and DB864 (5'-AGC TTG CAT AGG CGA GGT TGA GCT GCT AGT CCC AGC TGA GGA CGT AG-3') (SEQ ID NO: 8).

Example 2

Cell Culture

A primary human skin fibroblast cell line heterozygous at the IDUA locus (Q70X/W402X) and a normal fibroblast control that had been cultured a similar number of passages (P4-P6) were used in this study. Cells were cultured using Dulbecco's modified Eagle's medium supplemented with 10% fetal calf serum at 37° C. with 5% $CO^2$. All experiments were conducted with fibroblasts at 50-70% confluency. The concentration of gentamicin used in this study varied from 200 to 1000 μg/ml, with higher concentrations used with cells at a higher passage number.

Example 3

-L-iduronidase Activity and Immunoquantification Assays

Hurler fibroblasts (P4-P6) were grown in the presence of gentamicin (Gibco BRL) for 24 h. The cells were lysed using M-Per Mammalian Protein Extraction Reagent (Pierce) and the total protein concentration of each cellular extract was measured using the BCA method (Pierce). The assay measuring α-L-iduronidase activity was adapted from Hopwood et al. (37). The enzymatic activity from cell extracts containing ~20 μg of protein from Hurler cells and ~2.5 μg of protein from normal fibroblast extracts was measured following the addition of 80 nmol of 4-methyl-umbelliferone iduronide (FMU) (Calbiochem) substrate in a 50 μl reaction mixture. The reaction was incubated for 1 h at 37° C. after which the reaction was quenched by the addition of 1 ml of glycine-NaOH buffer pH 10.8. The fluorescence of the cleaved free FMU molecule was immediately measured at 365 nm excitation and 450 nm emission using a Shimadzu fluorometer and the amount of active iduronidase was expressed as nmol FMU cleaved/h/mg protein. A blank control demonstrated no change in fluorescence with the addition of the protein extraction reagent. The immuno-quantification assay was performed as previously described by Ashton et al. (10). The amount of α-L-iduronidase protein present in the Hurler cells was determined by interpolation using a standard curve generated from cell lysates prepared from normal human fibroblasts (where ~30 ng of α-L-iduronidase protein was present per mg of total cell protein).

Example 4

Measurement of Cellular GAG Levels

The glycosaminoglycan labeling assay was adapted from Thompson et al. (16). Normal and Hurler (P6) cells were cultured and labeled by the addition of 4 μCi/ml $^{35}SO_4$ to the culture medium. Radiolabeled extracts were prepared and subjected to serial hot EtOH extractions to determine the total counts incorporated into macromolecules (primarily protein and glycosaminoglycans). Unlabeled control samples processed in parallel were used to determine the total protein recovered from the precipitation procedure.

Example 5

Visualization of Lysosomal Abundance in Intact Cells

Normal and Hurler fibroblasts (P6) were grown on glass coverslips in polystyrene culture dishes in the presence or absence of 1000 μg/ml gentamicin for 48 hours. Following the addition of 40 mM HEPES to buffer the culture medium, 50 mM LysoTracker Red (Molecular Probes) was added for 1 hour at 37° C. The coverslips were then mounted on an Olympus inverted fluorescence microscope without fixation and visualized at 100× magnification.

Example 6

Hsp70 Western Blot

Normal fibroblasts were grown in the presence or absence of gentamicin for 24 h. Cellular extracts were then prepared by lysis in the presence of SDS sample buffer. Following a brief spin in a microfuge to remove insoluble debris, 25 μg of total protein was loaded onto a SDS-PAGE gel. Protein was transferred from the gel to Immobilon paper (Millipore) and incubated with rabbit anti-human Hsp70 antibody (Stress-Gen) followed by incubation with $^{125}$I-Protein A (Amersham). The abundance of Hsp70 present in each sample was quantitated by PhosphorImager analysis. A positive control for a maximal stress response was prepared by subjecting cells to a heat shock at 45° C. for 2 hours followed by an additional 2 hours incubation at 37° C. prior to harvesting.

Example 7

The Hurler Q70X and W402X Premature Stop Mutations are Susceptible to Gentamicin-mediated Suppression The suppression of stop mutations in mammalian cells is dependent on the context surrounding the stop codon (12,13). To determine whether aminoglycosides can suppress naturally occurring premature stop mutations that cause Hurler syndrome, IDUA cDNA templates containing the Q70X or W402X mutations were expressed in a rabbit reticulocyte lysate-coupled transcription/translation system in the presence of increasing concentrations of gentamicin. One can successfully visualize the IDUA W402X truncated peptide in the mammalian translation system expressed from the human IDUA cDNA construct. A dose-dependent increase in the amount of full-length α-L-iduronidase protein produced from the IDUA W402X cDNA was observed on addition of gentamicin to the translation mixture, with suppression of the premature stop codon occurring at a frequency of 4.6% in the presence of 10 µg/ml gentamicin (FIG. 1A). However, no visualization of the truncated Q70X product was possible due to its small size and lack of methionine codons.

Figure 1B:
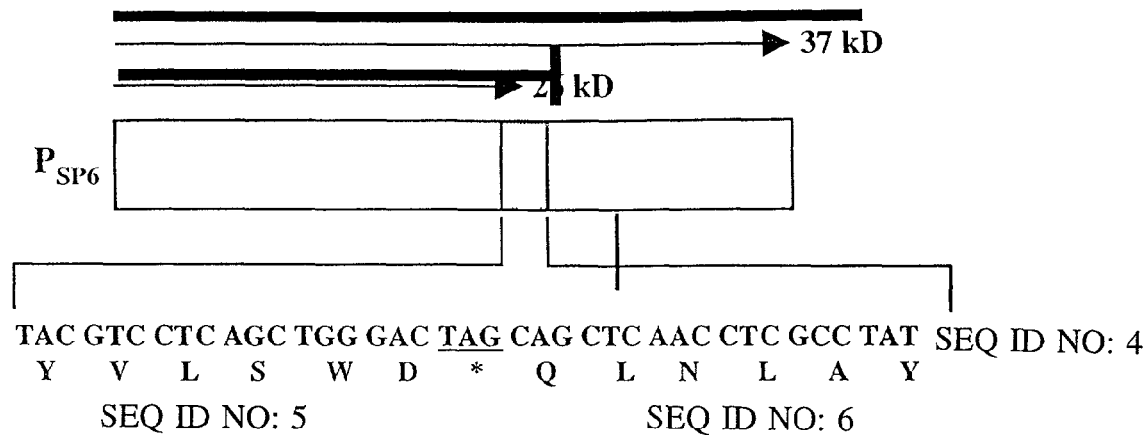
FIG. 1B shows proteins produced from the IDUA-Q70X reporter construct containing the Hurler syndrome Q70X stop mutation and the surrounding codons 64-76 of the IDUA gene when translation was carried out with increasing concentrations of gentamicin. Translation terminating at the Q70X mutation results in a 26 kDa product and suppression of the Q70X mutation yields a full length 37 kDa product. The level of suppression of the stop mutation (% full-length protein) represents the amount of full-length protein produced relative to the sum of the truncated and full-length proteins.
Figure 1B:
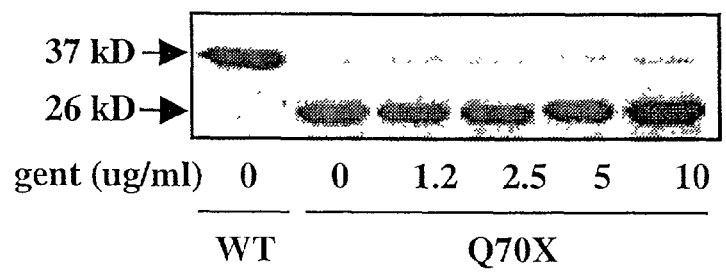
Figure 1B:
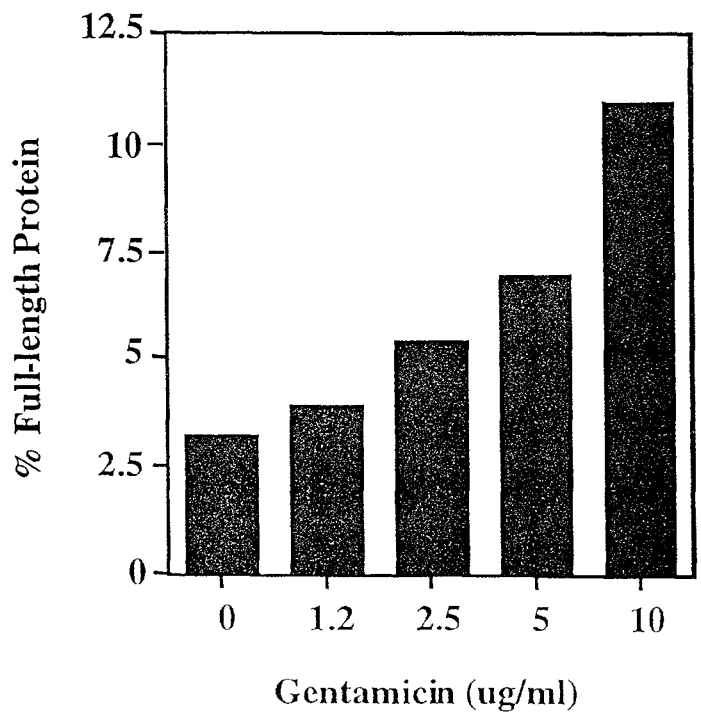

To determine whether gentamicin can suppress the Q70X mutation, the Q70X mutation and the six upstream and downstream codons were introduced into a construct previously developed to quantitate aminoglycoside-mediated suppression of stop mutations (FIG. 1B) (12). In this reporter system, efficient translation termination at the Q70X stop codon resulted in the production of a 27 kDa polypeptide and suppression of the Q70X mutation allowed the synthesis of a 37 kDa protein. Gentamicin suppressed the Q70X mutation to a level as high as 10.9%. These results demonstrate that both the IDUA Q70X and W402X premature stop mutations are susceptible to suppression by gentamicin.

Figure 2A:
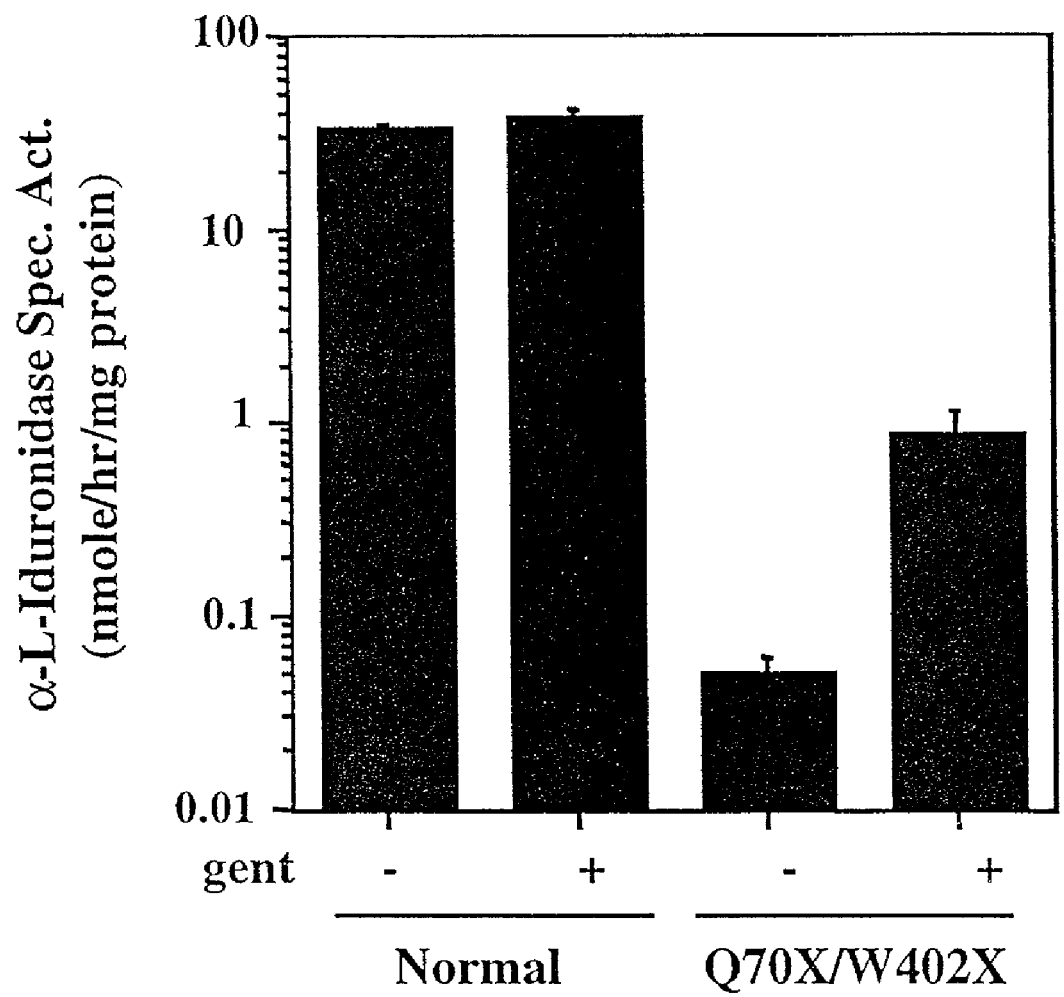
FIG. 2 shows gentamicin-mediated suppression of Hurler premature stop mutations produce functionally significant levels of α-L-iduronidase activity. Normal or Hurler fibroblast cell lines (P4) were cultured in the presence (+) or absence (−) of 200 μg/ml gentamicin for 24 h. The Hurler cell line was heterozygous for the Q70X and W402X IDUA mutations. The data are expressed as means ±SD.
Figure 2B:
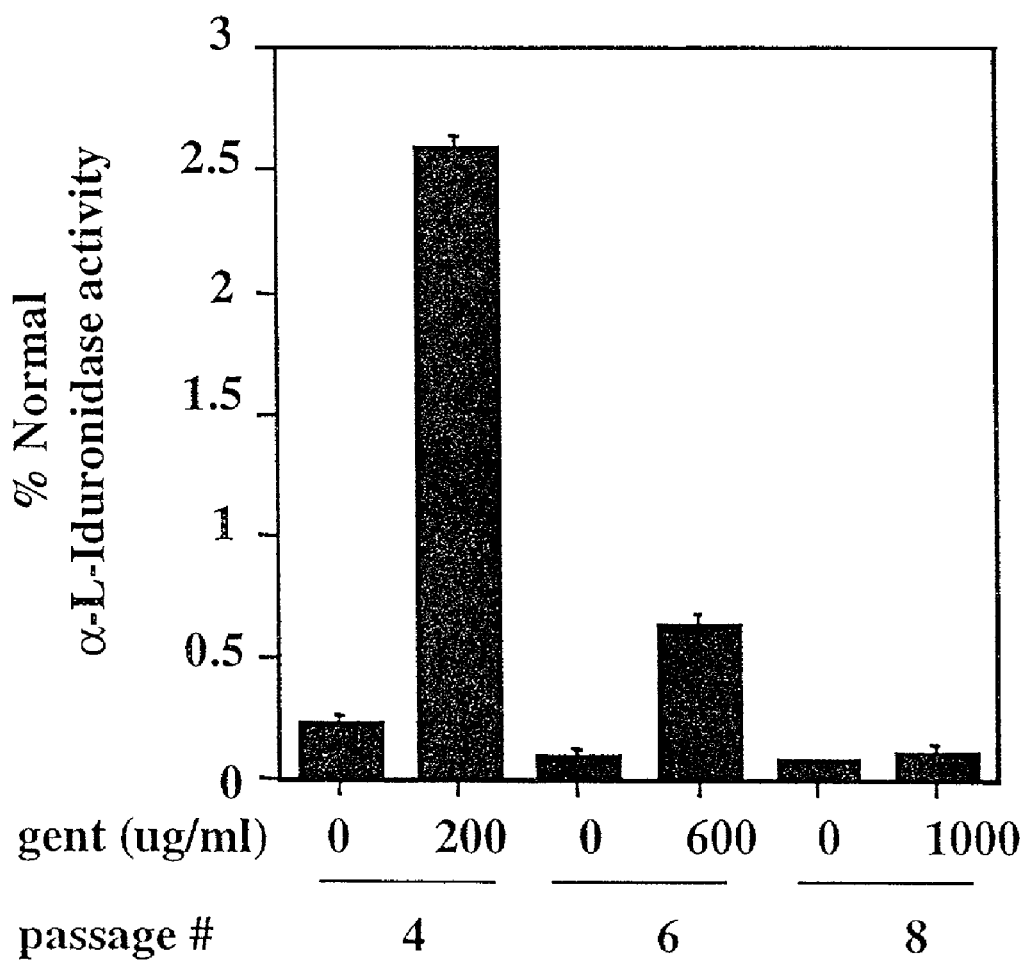

Example 8

α-L-iduronidase Activity and Protein are Partially Restored in Hurler Fibroblasts Following Gentamicin Treatment To determine whether the Q70X/W402X premature stop mutations in the IDUA gene can be suppressed in intact cells, Hurler fibroblasts (P4) were cultured in the presence of gentamicin for 24 h. Cellular extracts were then prepared and an α-L-iduronidase activity assay was performed. Gentamicin treatment increased the α-L-iduronidase-specific activity to 0.89 nmol/h/mg protein (FIG. 2A). This resulted in ~2.8% of the α-L-iduronidase specific activity that was measured in normal fibroblasts, a level previously reported to be sufficient to reduce or prevent the Hurler phenotype (10,11).

Figure 3:
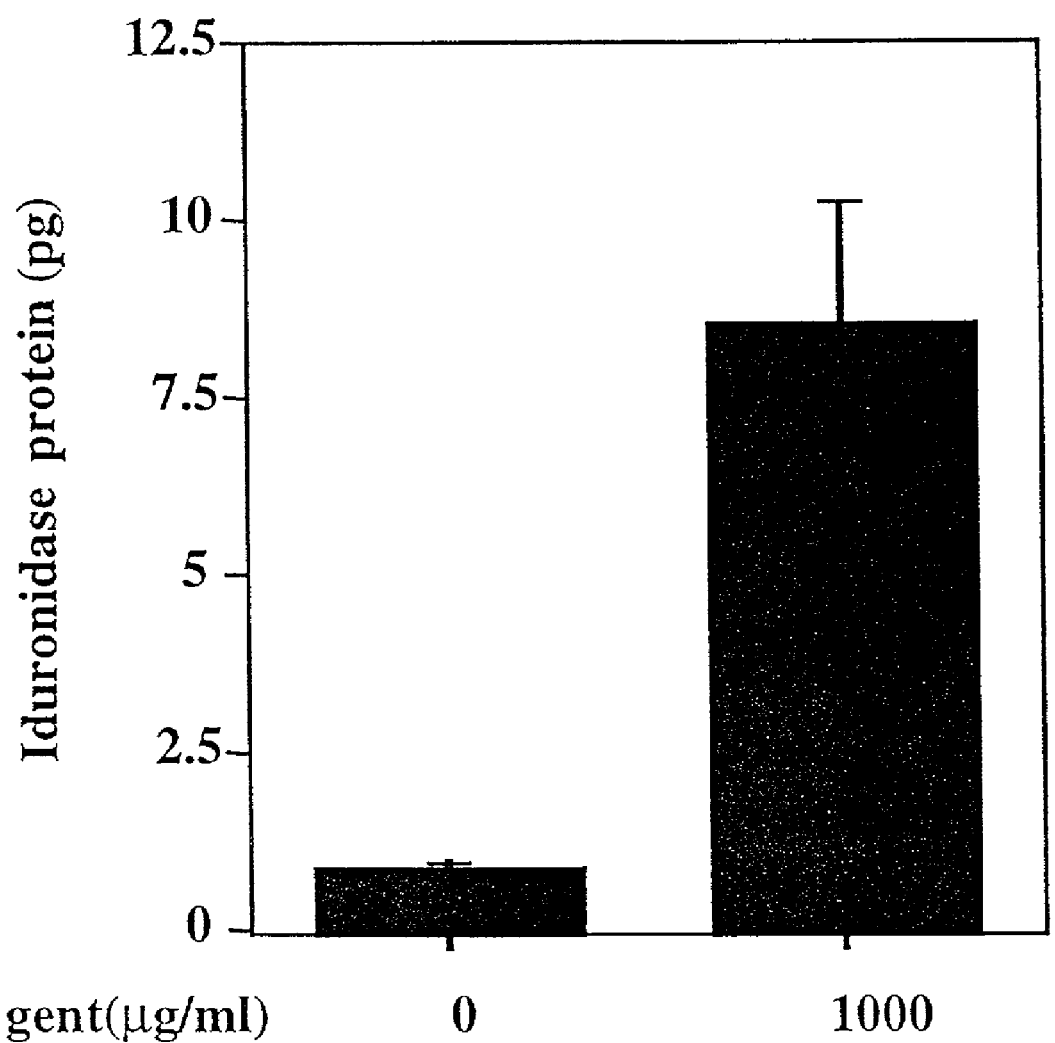
FIG. 3 shows gentamicin-mediated suppression of the Hurler Q70X/W402X mutations increases the level of α-L-iduronidase protein. A polyclonal-monoclonal sandwich immunoassay was carried out to determine the amount of α-L-iduronidase protein present in Q70X/W402X Hurler fibroblast cells cultured in the presence or absence of 1000 μg/ml gentamicin. The data are expressed as means ±SD.

Whether the increase in α-L-iduronidase activity observed after gentamicin treatment could also be correlated with an increase in the amount of α-L-iduronidase protein. Hurler fibroblasts (P6) were cultured in the presence or absence of gentamicin and the amount of α-L-iduronidase protein present in cell extracts was immunoquantified using a polyclonal-monoclonal sandwich immunoassay (10,15). The amount of α-L-iduronidase protein also increased significantly in gentamicin-treated Hurler fibroblasts (FIG. 3). The level of α-L-iduronidase protein observed in cells cultured in the absence of gentamicin (0.039 ng/mg total protein) is generally associated with a severe Hurler phenotype. In contrast, the amount of α-L-iduronidase in the gentamicin-treated Hurler cells was 0.41 ng/mg total protein, a level previously associated with a mild Hurler phenotype (10,15). Taken together, the results of both enzymatic and protein quantification assays indicate that gentamicin can suppress premature stop mutations in the IDUA gene and restore a functionally significant level of α-L-iduronidase activity and protein in cultured Hurler fibroblasts.

Example 9

Gentamicin-treated Hurler Fibroblasts have Decreased GAG Retention

Figure 4A:
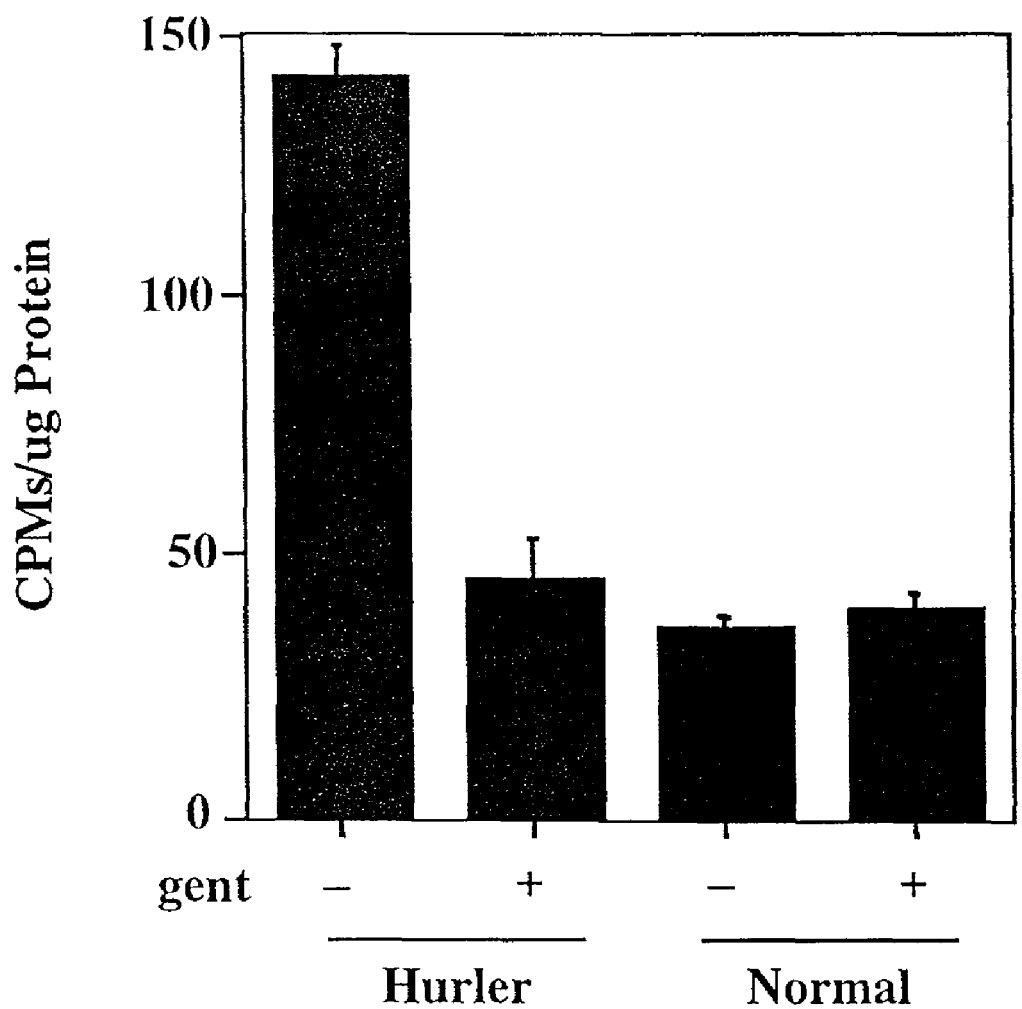
FIG. 4A shows normal and Hurler (Q70X/W402X) fibroblasts (P6) were cultured with $^{35}SO_4$ for 3 days and then cultured without $^{35}SO_4$ in the presence (+) or absence (−) of 1000 μg/ml gentamicin for 2 days. The level of glycosaminoglycans was then determined.

Previous studies have shown that Hurler fibroblasts accumulate a much higher level of GAGs than normal fibroblasts. This occurs because α-L-iduronidase activity is essential for lysosomal glycosaminoglycan degradation (6,16). To determine whether aminoglycoside-mediated suppression of stop mutations can restore a level of α-L-iduronidase activity that is sufficient to reduce glycosaminoglycan accumulation, normal and Hurler Q70X/W402X fibroblasts (P6) were cultured with $^{35}SO_4$ for 3 days to label the sulfated glycosaminoglycans synthesized during this period. The cells were then cultured in medium lacking $^{35}SO_4$ for 2 days in the presence or absence of gentamicin. After this chase period, the glycosaminoglycans were precipitated and the total $^{35}S$ incorporated into precipitable counts was quantitated. This value was then expressed relative to the total protein recovered in the precipitant. Under these conditions, untreated Hurler fibroblasts accumulated almost 4-fold more $^{35}S$-labeled glycosaminoglycans than normal fibroblasts (FIG. 4A). However, the amount of $^{35}S$-precipitable counts in the gentamicin-treated Hurler fibroblasts was reduced to a level similar to that observed in normal fibroblasts. These results indicate that the low level of α-L-iduronidase activity restored by gentamicin treatment can dramatically decrease the steady-state glycosaminoglycan level in Hurler fibroblasts.

Gentamicin mediates the suppression of stop mutations by binding to the decoding site of the small subunit rRNA (17). Based on this mechanism of action, the synthesis of full-length α-L-iduronidase should be maintained in Hurler fibroblasts only as long as gentamicin is available to facilitate the suppression of stop mutations in the IDUA gene. However, α-L-iduronidase activity should persist until the protein synthesized during gentamicin treatment is degraded.

Figure 4B:
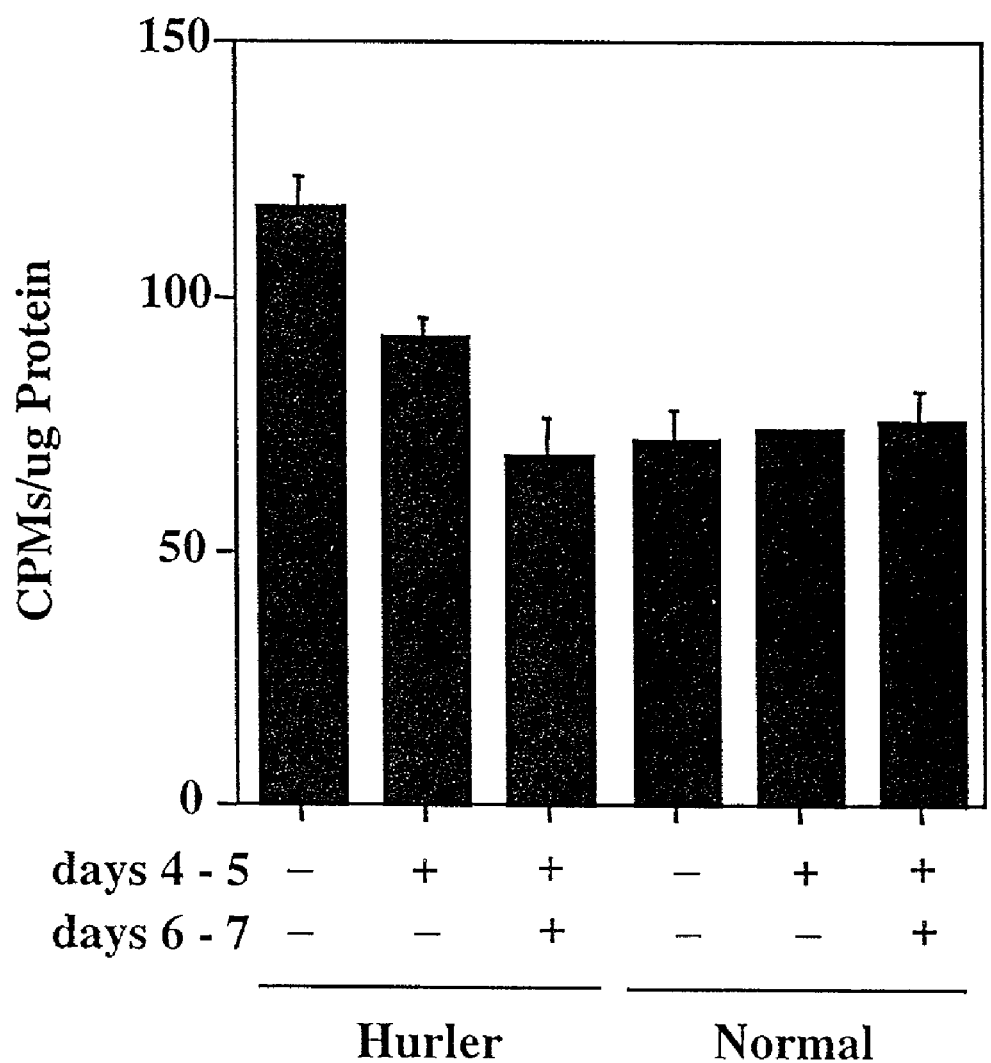
FIG. 4B shows normal and Hurler fibroblasts were cultured with $^{35}SO_4$ for 3 days (days 1-3) followed by a 48 h non-labeling (chase) period in the presence (+) or absence (−) of gentamicin (days 4-5). The cells were then incubated for an additional 2 days (days 6-7) with $^{35}SO_4$ to label newly synthesized glycosaminoglycans. The level of glycosaminoglycans was then determined. The data are expressed as means ±SD.

To determine whether a reduced glycosaminoglycan level can be sustained following the cessation of gentamicin treatment, normal and Hurler fibroblasts were labeled for 72 h with $^{35}SO_4$ (days 1-3) followed by a 48 h non-labeling (chase) period in the presence or absence of gentamicin (days 4-5). This was then followed by incubation for an additional 48 h (days 6-7) with $^{35}SO_4$ to label newly synthesized glycosaminoglycans (FIG. 4B). Following this procedure, the level of glycosaminoglycans was determined.

Using this protocol, the level of glycosaminoglycans in Hurler fibroblasts was 1.6-fold higher than normal when cells were cultured in the absence of gentamicin. When gentamicin treatment was present continuously during days 4-7, the glycosaminoglycan level in Hurler fibroblasts was maintained at a normal level. Finally, when gentamicin was present during days 4-5 but omitted during days 6-7, an intermediate level of glycosaminoglycan accumulation (1.3-fold higher than normal) in Hurler fibroblasts was observed. Since this level was significantly lower than was observed in the same cells cultured in the absence of gentamicin, one can conclude that gentamicin-treated cells can retain enough α-L-iduronidase activity to partially reduce glycosaminoglycan levels for at least 2 days following the cessation of gentamicin treatment.

Example 10

Gentamicin Treatment Restores Normal Lysosome Distribution and Morphology in Hurler Fibroblasts Hurler cells exhibit an increased abundance of lysosomes (termed vacuolation) and an abnormal lysosomal morphology as observed by light and electron microscopy (18). Since this morphological change is thought to occur as a direct consequence of the accumulation of glycosaminoglycans within lysosomes, whether gentamicin treatment could reverse this atypical lysosomal morphology was next examined.

Figure 5:
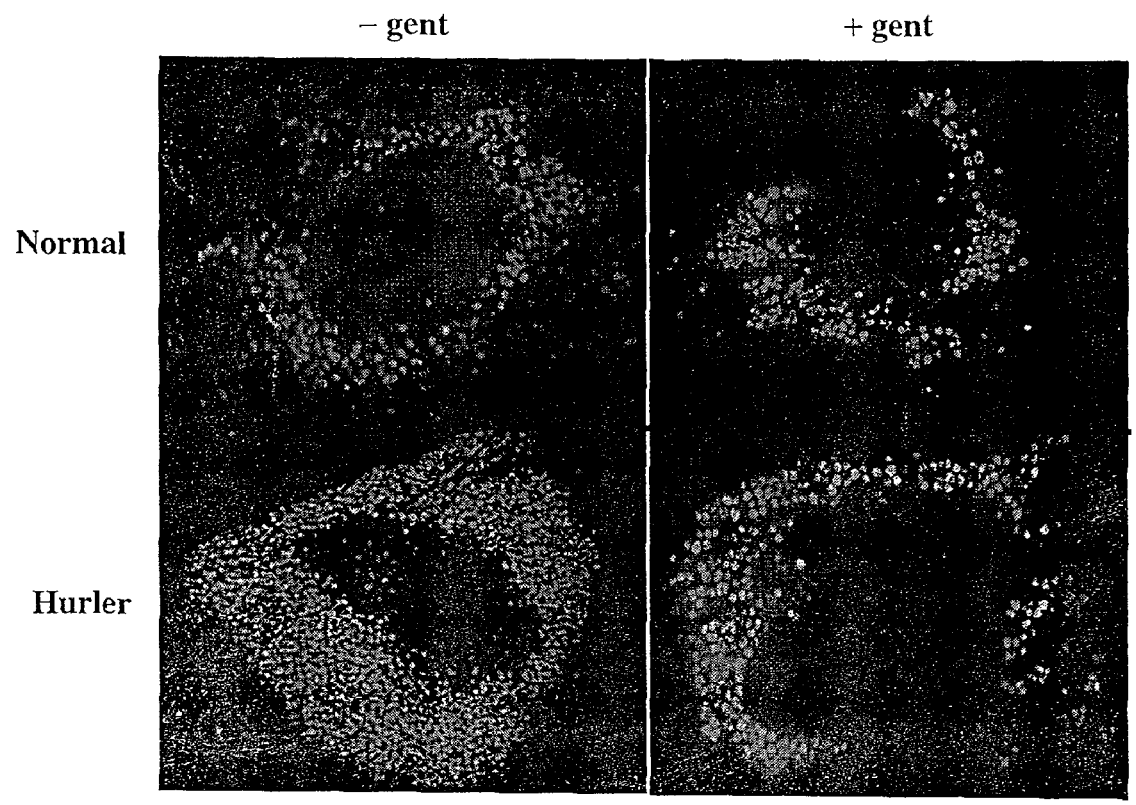
FIG. 5 shows normal lysosomal abundance is restored in Hurler fibroblasts after gentamicin treatment. Hurler (Q70X/W402X) and wild-type fibroblasts were grown on coverslips in the presence (+) or absence (−) of 1000 μg/ml gentamicin for 2 days. The cells were then incubated with the lysosome-specific fluorescent probe LysoTracker Red for 1 h at 37° C. and viewed at 100× magnification.

Normal and Hurler fibroblasts were cultured on glass coverslips in the presence or absence of gentamicin for 2 days. The cells were then incubated for 1 h at 37° C. with LysoTracker Red, a fluorescent dye that is endocytosed into lysosomes. Untreated Hurler fibroblasts contain more lysosomes than normal cells and these compartments appeared smaller in size than the lysosomes observed in normal cells (FIG. 5). In contrast, the majority of gentamicin-treated Hurler fibroblasts contained fewer lysosomes that were normal in appearance. The staining pattern observed in the gentamicin-treated Hurler fibroblasts resembled the pattern observed in wild-type cells in ≧70% of cells examined, indicating that gentamicin treatment largely restores a normal pattern of lysosome distribution and morphology in Hurler fibroblasts.

Example 11

Gentamicin Concentrations that Suppress Premature Stop Mutations Do Not Induce a Strong Stress Response A major concern related to the pharmacological suppression of premature stop mutations is the possibility that native stop codons present at the end of normal cellular mRNAs may also be suppressed. The global suppression of stop codons at the ends of genes could be expected to produce many proteins with C-terminal extensions that may lead to protein misfolding. Such widespread protein misfolding should induce a stress response, leading to an increase in the steady-state level of the molecular chaperone Hsp70. Hsp70 is induced during many different conditions and acts to prevent the aggregation of misfolded proteins that may accumulate as a result of cellular stress (19).

Figure 6:
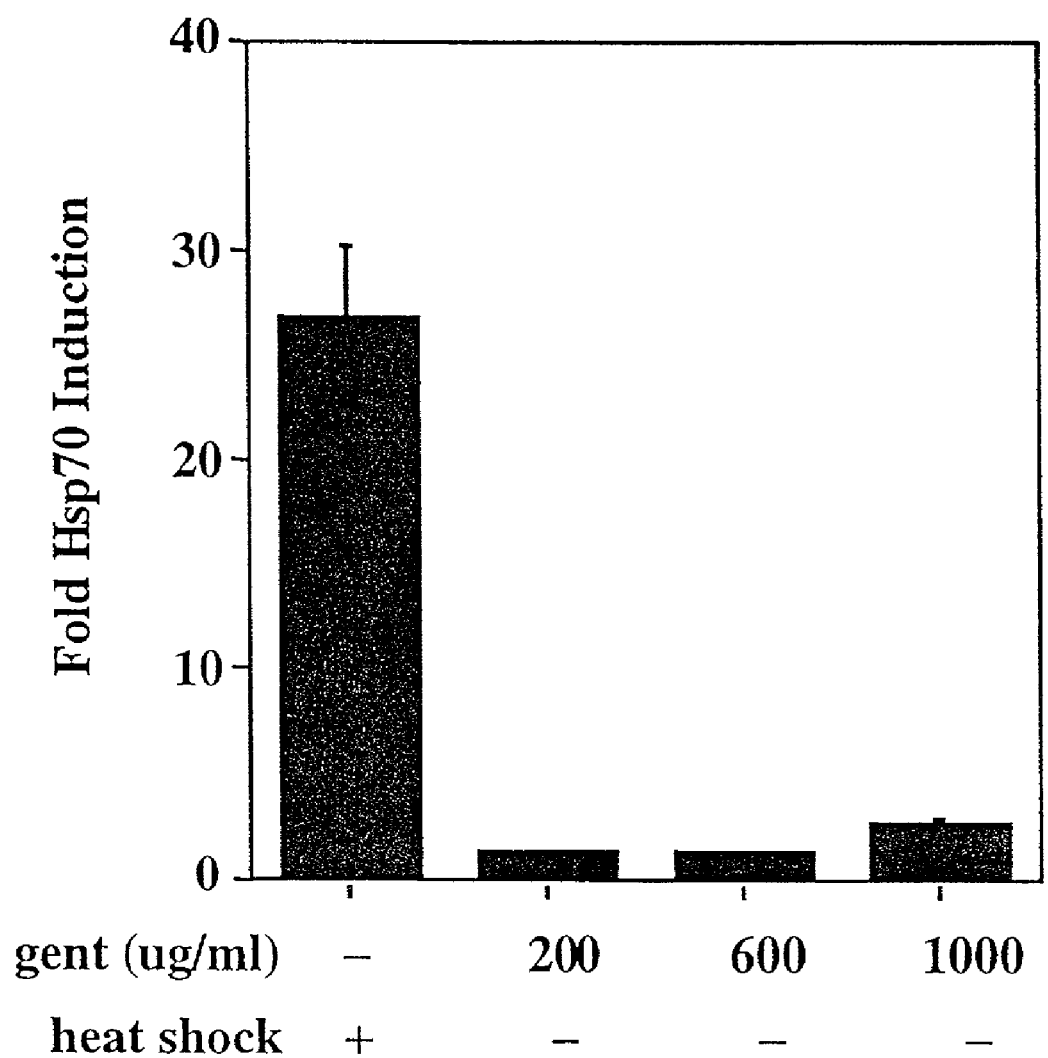
FIG. 6 shows gentamicin treatment does not induce a strong cellular stress response. The abundance of the inducible form of Hsp70 was measured by western blot in normal fibroblasts (P6) that were cultured with the indicated concentrations of gentamicin. The results are expressed as the fold increase in Hsp70 that resulted from gentamicin treatment. To determine the increase in the Hsp70 level during a strong stress response, fibroblasts were subjected to a heat shock as described below. The data are expressed as means ±SD.

To determine whether the gentamicin concentrations used in this study can induce a stress response, normal human fibroblasts (P6) were cultured in the presence of increasing levels of gentamicin and monitored the induction of Hsp70 by western blot analysis. A parallel flask of cells was subjected to heat shock to determine the maximal Hsp70 level obtained during a full-scale stress response (FIG. 6).

Small progressive increases in Hsp70 levels were observed with increasing gentamicin concentrations. A 1.2-fold increase was found in the Hsp70 level in cells cultured in the presence of 200 μg/ml gentamicin, a 1.3-fold increase in cells cultured in the presence of 600 μg/ml gentamicin and a 2.7-fold increase in cells cultured with 1000 μg/ml gentamicin. However, this maximal level of Hsp70 remained 10-fold below the level of Hsp70 observed in cells exposed to heat shock. Consistent with these results, it was also found that this range of aminoglycosides did not have a significant effect on cell viability or total protein synthesis rates (data not shown). These results indicate that gentamicin treatment under the conditions used in this study induce only a very modest stress response.

Example 12

Poly-L-aspartate can Stimulate the Ability of Gentamicin to Suppress Premature Stop Mutations While Reducing the Toxic Side Effects of Aminoglycosides Previous studies have shown that the co-administration of poly-anionic compounds can significantly reduce the nephrotoxicity and ototoxicity of aminoglycosides in vitro and in vivo. It is thought that these compounds may mediate this protection by reducing electrostatic interactions between the aminoglycosides and acidic phospholipid headgroups in the lysosomal membrane. For example, the co-administration of poly-L aspartic acid (J. Pharm. Exp. Ther. 262:424-432, 1992; Life Sci. 56: 1877-1887, 1995) or daptomycin (Antimicrob. Agents Chemother. 38: 1027-1035, 1994) has been shown to reduce aminoglycoside-induced nephrotoxicity in animal models. These findings suggest that it may be possible to avoid the toxic side-effects of aminoglycosides as recently suggested (Antimicrob. Agents Chemother. 43: 1003-1012, 1999) while still maintaining their therapeutic effects.

Figure 7:
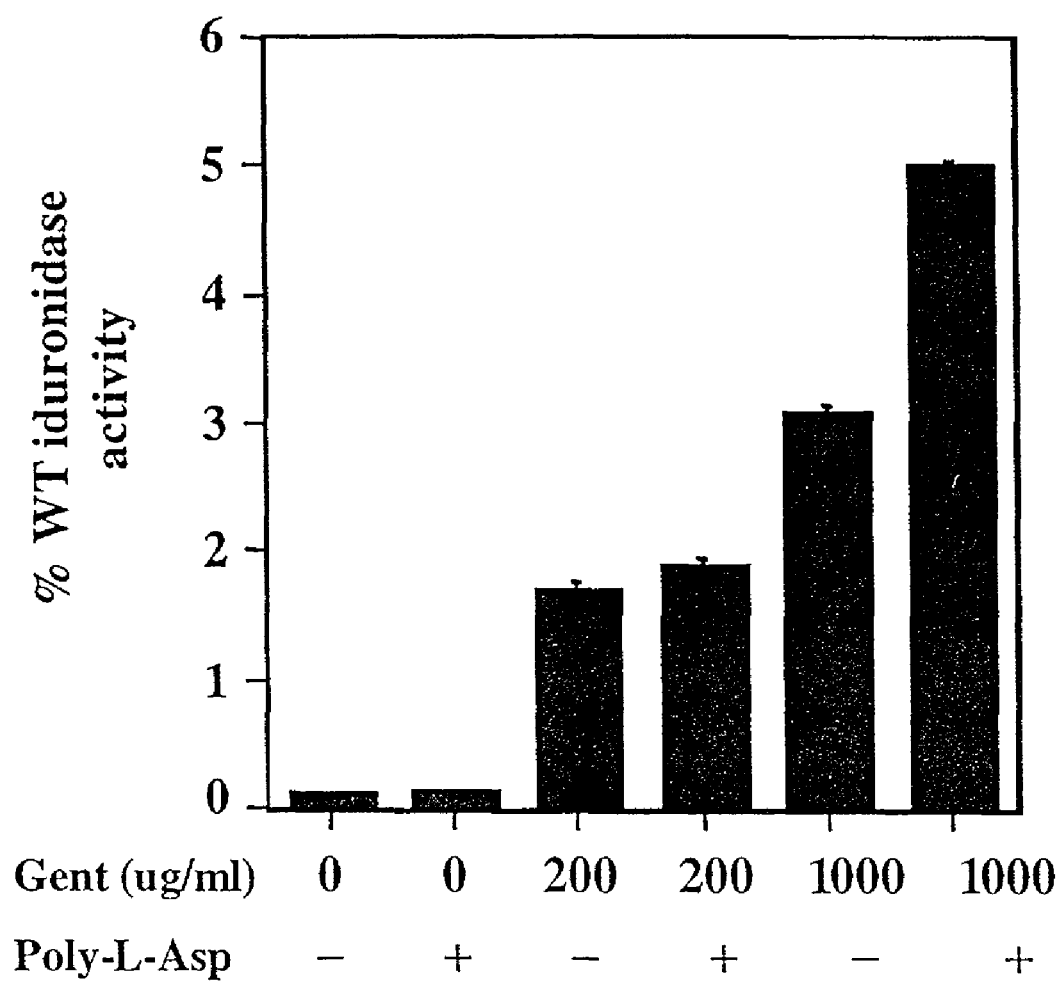
FIG. 7 shows the co-administration of poly-L-aspartate and gentamicin can further stimulate the suppression of premature stop mutations. The data are expressed as the percent of wild type iduronidase activity expressed in Hurler fibroblasts (P4) in the presence of varying concentrations of gentamicin with or without the addition of 250 μg/ml poly-L-aspartate. The data are expressed as means ±SD.

To determine the affect of poly-L-aspartate on the aminoglycoside-mediated suppression of stop codons, the ability of gentamicin to stimulate readthrough when administered in the presence of poly-L-aspartate was next examined. While the co-administration of poly-L-aspartate did not affect the level of readthrough at low gentamicin concentrations, poly-L-aspartate increased the α-L-iduronidase activity by 60-70% in Hurler fibroblasts at high gentamicin concentrations (FIG. 7). At this gentamicin concentration, a molar ratio of poly-L-aspartate: gentamicin of 1:100 was used (corresponding to a mass ratio of 1:5).

Poly-L-aspartate may mediate this effect by one of two mechanisms. It may interact directly with gentamicin through electrostatic interactions and stimulate its uptake into the cell. Alternatively, the poly-L-aspartate may prevent the association of gentamicin with non-productive binding sites such as lipid headgroups (either on the cell surface or inside the cell) so that more gentamicin is available to interact with the translation machinery.

Discussion

Three approaches are currently considered promising avenues for the treatment of Hurler syndrome patients: bone marrow transplantation, enzyme replacement therapy and gene therapy. Hurler syndrome patients who received allogenic bone marrow transplantation exhibited a significant increase in serum α-L-iduronidase activity, a marked decrease in urinary glycosaminoglycan levels and a significant improvement in survivability. Diverse symptoms of the somatic disease such as liver and heart disease, hearing problems and dysmorphic features were also greatly diminished in treated patients. Skeletal abnormalities generally persisted but neurological improvement occurred in some patients (20-23). Although these results are extremely promising, the potential complications that accompany the use of immunosuppressive drugs to prevent graft rejection make this approach less than ideal.

Another promising treatment for patients with Hurler syndrome is enzyme replacement therapy, or the periodic intravenous administration of purified α-L-iduronidase. Recently, Hurler patients administered weekly infusions of recombinant α-L-iduronidase were found to exhibit a marked reduction of glycosaminoglycan excretion and liver disease and improvements in joint mobility and heart function (24). Possible drawbacks to this approach include the lack of normal post-translational modification on the recombinant protein used, which could reduce cellular uptake and increase the chance of an immune response. Although limited immune responses have occurred in some treated patients, these responses were not severe enough to force the termination of treatment and this approach continues to show promise.

Finally, gene therapy has also been explored as a treatment for Hurler syndrome patients. Hurler fibroblasts and $CD34^+$ bone marrow cells transduced with recombinant adeno-associated virus or retroviral constructs containing the human IDUA cDNA showed high, extended α-L-iduronidase expression and clearance of glycosaminoglycans in vitro (25-27). However, the use of gene therapy approaches as a standard treatment for Hurler syndrome patients may remain years away.

The present invention indicates that nonsense-suppression therapy may provide a novel, non-invasive option for the treatment of Hurler syndrome patients carrying premature stop mutations in the IDUA gene. Previous studies have shown that low levels of α-L-iduronidase activity and protein are correlated with a less severe MPS I phenotype (10,11,15). In the current study, gentamicin treatment was capable of restoring 2.5-3% of normal α-L-iduronidase activity in cultured Hurler fibroblasts. Also, the level of α-L-iduronidase protein in gentamicin-treated Hurler cells was 0.41 ng/mg total protein, a level of enzyme that has been correlated with a mild Hurler phenotype (10,15). Thus, both enzymatic and immunological criteria suggest that gentamicin treatment can restore a sufficient level of α-L-iduronidase to reduce the severity of the MPS I phenotype in cultured cells from Hurler patients that harbor premature stop mutations in the IDUA gene.

Another advantage of aminoglycoside therapy is that proteins produced by this approach should transit normally through the secretory pathway, resulting in normal glycosylation of the protein within the ER and Golgi apparatus. When combined with the overall low level of α-L-iduronidase produced by the suppression of a premature stop mutation, the possibility of an immune response induced by the restored expression of α-L-iduronidase should be low in MPS I patients. Since the protein will probably not carry the normal amino acid at the position where the stop mutation occurred, it is also possible that the half-life of the protein may be altered. However, cells labeled for 2 days after the removal of gentamicin could sustain reduced glycosaminoglycan levels. This indicates that the α-L-iduronidase produced by readthrough is relatively stable during this period. One potential limitation of this approach as a treatment for Hurler syndrome is the low permeability of gentamicin across the blood-brain barrier, which may prohibit the correction of the neurological manifestations of the disease (28). Gentamicin-mediated suppression of stop mutations in the IDUA gene that reduce glycosaminoglycan levels in the brain can be examined in an animal model.

In studies over the last few years, it was found that aminoglycoside permeability varies significantly between different cell types. This is readily apparent from previous in vitro studies with CF and muscular dystrophy models, where the range of aminoglycoside concentrations used varied from 10 to 1000 μg/ml (1,2,5). In this study, evidence was obtained suggesting that the permeability or efflux of gentamicin in primary fibroblasts may change with increasing passage number. It has been reported that changes in membrane permeability occur with continued passage of cultured primary fibroblasts (14). In an attempt to bypass these difficulties, whether commonly used permeabilizing agents could increase the entry of gentamicin into Hurler fibroblasts was examined. Unfortunately, neither dimethylsulfoxide (DMSO) nor mannitol were found to increase the level of α-L-iduronidase activity produced by gentamicin treatment (data not shown). However, the addition of poly-L-aspartate to the growth medium was found to increase the ability of gentamicin to stimulate α-L-iduronidase activity in Hurler fibroblasts at high gentamicin concentrations. This suggests that poly-L-aspartate may be capable of stimulating the uptake of aminoglycosides into the cell, possibly through a mechanism involving fluid phase endocytosis. Because of these permeability problems associated with cultured primary cells, the aminoglycoside concentrations routinely used in these in vitro studies generally exceeded the concentrations that would be useful in a clinical setting. However, pilot studies have shown that aminoglycosides can partially restore CFTR expression through the suppression of stop mutations when administered at clinically relevant doses (3,4). When combined with the low threshold for correction that appears to be associated with Hurler syndrome, these findings indicate that this approach may provide a viable treatment for MPS I patients with Hurler syndrome.

A hurdle to long-term gentamicin therapy is the nephrotoxicity and ototoxicity that can be associated with aminoglycoside treatment in some patients. However, several studies have shown that the cause of aminoglycoside-induced toxicity appears to be unrelated to their ability to suppress translation termination and our finding that gentamicin treatment does not induce a stress response supports those results (29, 30). Numerous studies have reported that the co-administration of polyanionic compounds appears to reduce aminoglycoside-induced nephrotoxicity in rats (31,32) and antioxidant compounds have been found to relieve ototoxicity in guinea pigs (33,34). In addition, structural changes within aminoglycosides (including gentamicin) have been shown to reduce their nephrotoxic effects in a rat model (35,36). This suggests that it may be possible to design new compounds that may be able to suppress premature stop mutations without inducing the toxic side effects associated with aminoglycosides. Additional studies are needed to determine whether aminoglycoside suppression of premature stop mutations can be developed into a successful long-term treatment for patients with Hurler syndrome.

The following references were cited herein:
1. Bedwell, et al., (1997) Suppression of a CFTR premature stop mutation in a bronchial epithelial cell line. *Nature Med.*, 3, 1280-1284.
2. Howard, et al., (1996) Aminoglycoside antibiotics restore CFTR function by overcoming premature stop mutations. *Nature Med.*, 2, 467-469.
3. Wilschanski, et al., (2000) A pilot study of the effect of gentamicin on nasal potential difference measurements in cystic fibrosis patients carrying stop mutations. *Am. J. Respir. Crit. Care Med.*, 161, 860-865.
4. Clancy, et al., (2001) Gentamicin suppresses premature stop mutations in cystic fibrosis patients. *Am. J. Respir. Crit. Care Med.*, in press.
5. Barton-Davis, et al., (1999) Aminoglycoside antibiotics restore dystrophin function to skeletal muscles of mdx mice. *J. Clin. Invest.*, 104, 375-381.

6. Neufeld, et al., (1989) The mucopolysaccharidoses. In Beaudet, A. L., Sly, W. S. and Valle, D. (eds), *The Metabolic Basis of Inherited Disease*. McGraw Hill, New York, N.Y., pp. 1565-1587.
7. Whitley, C. B. (1993) Inheritable disorders of connective tissue. In Beighton, P. (ed.), *Inheritable Disorders of Connective Tissue*. Mosley, St Louis, Mo., pp. 367-499.
8. Bunge, et al., (1994) Mucopolysaccharidosis type I: identification of 8 novel mutations and determination of the frequency of the two common _-L-iduronidase mutations (W402X and Q70X) among European patients. *Hum. Mol. Genet.*, 3, 861-866.
9. Aronovich, et al., (1996) Molecular genetic defect underlying _-L-iduronidase pseudodeficiency. *Am. J. Hum. Genet.*, 58, 75-85.
10. Ashton, et al., (1992) Immunoquantification and enzyme kinetics of _-L-iduronidase in cultured fibroblasts from normal controls and mucopolysaccharidosis type I patients. *Am. J. Hum. Genet.*, 50, 787-794.
11. Whitley, et al., (1987) A nonpathologic allele (Iw) for low α-L-iduronidase enzyme activity vis-a-vis prenatal diagnosis of Hurler syndrome. *Am. J. Med. Genet.*, 28, 233-243.
12. Manouvkova, et al., (2000) Aminoglycoside antibiotics mediate context-dependent suppression of termination codons in a mammalian translation system. *RNA*, 6, 1044-1055.
13. McCaughan, et al., (1995) Translational termination efficiency in mammals is influenced by the base following the stop codon. *Proc. Natl Acad. Sci. USA*, 92, 5431-5435.
14. Schroeder, et al., (1984) Age-related alterations in cultured human fibroblast membrane structure and function. *Mech. Ageing Dev.*, 25, 365-389.
15. Bunge, et al., (1998) Genotype-phenotype correlations in mucopolysaccharidosis type I using enzyme kinetics, immunoquantification and in vitro turnover studies. *Biochim. Biophys. Acta*, 1407, 249-256.
16. Thompson, et al., (1991) Enzymatic diagnosis of selected mucopolysaccharidoses: Hunter, Morquio Type A, and Sanfilippo Types A, B, C and D, and procedures for measurement of $^{35}SO_4$-glycosaminoglycans. In: Frits A. Hommes. Ed. *Techniques in Diagnostic Human Biochemical Genetics: A Laboratory Manual* Wiley-Liss, New York. pp. 567-586.
17. Yoshizawa, et al., (1998) Structural origins of gentamicin antibiotic action. *EMBO J.*, 22, 6437-6448.
18. Bioulac, et al., (1975) The diagnosis of mucopolysaccharidoses by electron microscopy of skin biopsies. *J. Cutan. Pathol.*, 2, 179-190.
19. Agashe, et al., (2000) Roles of molecular chaperones in cytoplasmic protein folding. *Semin. Cell Dev. Biol.*, 11, 15-25.
20. Whitley, et al., (1993) Long-term outcome of Hurler syndrome following bone marrow transplantation. *Am. J. Med. Genet.*, 46, 209-218.
21. Guffon, et al., (1998) Follow-up of nine patients with Hurler syndrome after bone marrow transplantation. *J. Pediatr.*, 133, 119-125.
22. Hopwood, et al., (1993) Long-term clinical progress in bone marrow transplanted mucopolysaccharidosis type I patients with a defined genotype. *J. Inherit. Metab. Dis.*, 16, 1024-1033.
23. Peters, et al., (1996) Outcome of unrelated donor bone marrow transplantation in 40 children with Hurler syndrome. *Blood*, 87, 4894-4902.
24. Kakkis, et al., (2000) Enzyme replacement therapy in MPS I: current status of patients up to 104 weeks of therapy. In *Joint Meeting of International Symposium on Innovative Therapies and the 6th International Symposium on Mucopolysaccharidosis and Related Diseases*. Minneapolis, Minn., p. 23.
25. Hartung, et al., (1999) Enzymatic correction and crosscorrection of mucopolysaccharidosis type I fibroblasts by adeno-associated virus-mediated transduction of the α-L-iduronidase gene. *Hum. Gene Ther.*, 10, 2163-2172.
26. Fairbairn, et al., (1996) Long-term in vitro correction of α-L-iduronidase deficiency (Hurler syndrome) in human bone marrow. *Proc. Natl Acad. Sci. USA*, 93, 2025-2030.
27. Huang, et al., (1997) Retrovirus-mediated transfer of the human α-L-iduronidase cDNA into human hematopoietic progenitor cells leads to correction in trans of Hurler fibroblasts. *Gene Ther.*, 4, 1150-1159.
28. Strausbaugh, L. J. and Brinker, G. S. (1983) Effect of osmotic blood-brain barrier disruption on gentamicin penetration into the cerebrospinal fluid and brains of normal rabbits. *Antimicrob. Agents Chemother.*, 24, 147-150.
29. Brummett, et al., (1989) Aminoglycoside-induced hearing loss in humans. *Antimicrob. Agents Chemother.*, 33, 797-800.
30. Mingeot-Leclercq, et al., (1999) Aminoglycosides: nephrotoxicity. *Antimicrob. Agents Chemother.*, 43, 1003-1012.
31. Kishore, et al., (1992) Comparative assessment of poly-L-aspartic and poly-L-glutamic acids as protectants against gentamicin-induced renal lysosomal phospholipidosis, phospholipiduria and cell proliferation in rats. *J. Pharmacol. Exp. Ther.*, 262, 424-432.
32. Thibault, et al., (1995) Protection against gentamicin nephrotoxicity by daptomycin in nephrectomized rats. *Life Sci.*, 56, 1877-1887.
33. Basile, et al., (1996) N-methyl-D-aspartate antagonists limit aminoglycoside antibiotic-induced hearing loss. *Nature Med.*, 2, 1338-1343.
34. Song, et al., (1998) Iron chelators protect from aminoglycoside-induced cochleo- and vestibulo-toxicity. *Free Radic. Biol. Med.*, 25, 189-195.
35. Schepdael, et al., (1991) New derivatives of kanamicin B obtained by modifications and substitutions in position 6'. 1. Synthesis and microbiological evaluation. *J. Med. Chem.*, 34, 1468-1475.
36. Maldague, et al., (1984) A 2' guanidyl derivative of gentamicin (S86451) with reduced nephrotoxicity: studies at low and medium dose levels in the rat. Arch. Toxicol., 7, (suppl.), 455-458.
37. Hopwood, et al., (1979) A fluorometric assay using 4-methylumbelliferyl α-L-iduronide for the estimation of α-L-iduronidase activity and the detection of Hurler and Scheie syndromes. *Clin. Chim. Acta*, 92, 257-265.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating mucopolysaccharidosis I in an individual in need thereof, wherein mucopolysaccharidosis I is associated with a loss of an enzymatic activity due to the presence of a naturally occurring premature stop mutation, said method comprising administering to the individual a therapeutically effective dose of gentamicin, wherein the therapeutically effective dose of gentamicin increases the enzymatic activity through suppression of the naturally occurring premature stop mutation.

2. The method of claim 1, wherein the therapeutically effective dose of gentamicin is from about 1 mg/kg to about 500 mg/kg.

3. The method of claim 1, wherein mucopolysaccharidosis I is selected from Hurler disease, Hurler/Scheie disease or Scheie disease.

4. The method of claim 1, wherein mucopolysaccharidosis I is Hurler disease.

5. The method of claim 4, wherein the naturally occurring premature stop mutation is an IDUA-Q70X stop mutation or an IDUA-W402X stop mutation.

6. The method of claim 1, further comprising administering to the individual an amount of a poly-anionic compound, wherein the amount of the poly-anionic compound is effective to further increase gentamicin suppression of the naturally occurring premature stop mutation.

7. The method of claim 1, further comprising administering to the individual an amount of poly-L-aspartate, wherein the amount of poly-L-aspartate is effective to further increase gentamicin suppression of the naturally occurring premature stop mutation, and wherein the poly-L-aspartate is administered at a molar ratio of poly-L-aspartate to gentamicin of about 1:100.

8. The method of claim 4, wherein the loss of an enzymatic activity due to the presence of a naturally occurring premature stop mutation is loss of α-L-iduronidase activity and suppression of the naturally occurring premature stop mutation increases α-L-iduronidase activity.

9. The method of claim 8, wherein the therapeutically effective dose of gentamicin is from about 1 mg/kg to about 500 mg/kg.

10. The method of claim 8, wherein the naturally occurring premature stop mutation is an IDUA-Q70X stop mutation or an IDUA-W402X stop mutation.

11. The method of claim 8, further comprising administering an amount of a poly-anionic compound, wherein the amount of the poly-anionic compound is effective to further increase gentamicin suppression of the naturally occurring premature stop mutation.

12. The method of claim 8, further comprising administering an amount of poly-L-aspartate, wherein the amount of poly-L-aspartate is effective to further increase gentamicin suppression of the naturally occurring premature stop mutation, and wherein the poly-L-aspartate is administered at a molar ratio of poly-L-aspartate to gentamicin of about 1:100.

13. The method of claim 4, wherein the loss of an enzymatic activity due to the presence of a naturally occurring premature stop mutation is loss of α-L-iduronidase activity, suppression of the naturally occurring premature stop mutation increases α-L-iduronidase activity and such increase alleviate at least one of the following conditions associated with Hurler disease: stiffness in the joints, skeletal abnormalities, corneal clouding, heart disease, liver disease or mental deterioration.

14. The method of claim 13, wherein the therapeutically effective dose of gentamicin is from about 1 mg/kg to about 500 mg/kg.

15. The method of claim 13, wherein the naturally occurring premature stop mutation is an IDUA-Q70X stop mutation or an IDUA-W402X stop mutation.

16. The method of claim 13, further comprising administering an amount of a poly-anionic compound, wherein the amount of the poly-anionic compound is effective to further increase gentamicin suppression of the naturally occurring premature stop mutation.

17. The method of claim 13, further comprising administering an amount of poly-L-aspartate, wherein the amount of poly-L-aspartate is effective to further increase gentamicin suppression of the naturally occurring premature stop mutation, and wherein the poly-L-aspartate is administered at a molar ratio of poly-L-aspartate to gentamicin of about 1:100.

* * * * *